United States Patent
Bito et al.

(10) Patent No.: US 7,552,062 B2
(45) Date of Patent: Jun. 23, 2009

(54) METHOD AND SYSTEM FOR CLINICAL PROCESS ANALYSIS

(75) Inventors: Yoshitaka Bito, Kawaguchi (JP); Shigeo Sumino, Fuchu (JP); Hajime Sasaki, Kawasaki (JP); Hitoshi Matsuo, Musashino (JP); Yoshiyuki Nakayama, Kawasaki (JP)

(73) Assignee: Hitachi, Ltd., Tokyo (JP)

( * ) Notice: Subject to any disclaimer, the term of this patent is extended or adjusted under 35 U.S.C. 154(b) by 1217 days.

(21) Appl. No.: 10/167,450

(22) Filed: Jun. 13, 2002

(65) Prior Publication Data

US 2003/0048265 A1 Mar. 13, 2003

(30) Foreign Application Priority Data

Sep. 11, 2001 (JP) ............................. 2001-274421

(51) Int. Cl.
*G06Q 50/00* (2006.01)
(52) U.S. Cl. .................. 705/2; 705/3; 700/29; 700/30; 700/32; 700/36; 700/28; 717/107; 717/120; 706/45
(58) Field of Classification Search .................. 705/2, 705/3, 4; 700/29, 30, 32, 36, 28; 717/107, 717/120; 706/45
See application file for complete search history.

(56) References Cited

U.S. PATENT DOCUMENTS

| | | | | |
|---|---|---|---|---|
| 5,953,704 A * | 9/1999 | McIlroy et al. | .................. | 705/2 |
| 6,061,657 A * | 5/2000 | Whiting-O'Keefe | ........... | 705/2 |
| 6,230,142 B1 * | 5/2001 | Benigno et al. | ................. | 705/3 |
| 6,266,645 B1 * | 7/2001 | Simpson | ........................ | 705/3 |
| 6,468,210 B1 * | 10/2002 | Iliff | ............................ | 600/300 |
| 6,754,883 B2 * | 6/2004 | DeBusk et al. | .............. | 717/107 |
| 7,392,201 B1 * | 6/2008 | Binns et al. | ..................... | 705/4 |
| 2003/0065535 A1 * | 4/2003 | Karlov et al. | .................. | 705/2 |

FOREIGN PATENT DOCUMENTS

| | | |
|---|---|---|
| JP | 4-102969 | 8/1990 |
| JP | 2001-117930 | 10/1999 |

OTHER PUBLICATIONS

Navigate a clinical pathway for uncomplicated MI patients, Karen T. McKinsey; Denise M Boren; Judith A Fidellow, Nursing Management; Oct. 1999; 30;10.*
Intelligent Image processing, issued in 1994 from Shokodo Co., Ltd. pp. 61-64.
Yoshitaka Bito, Robert Kero, Hitoshi Matsuo, Yoichi Shintani, Michael Silver, "Interactively Visualizing Data Warehouses", Journal of Healthcare Information Management, Vo. 15, No. 2, Summer 2001, pp. 133-142.
U.S. Appl. No. 09/687,058, filed on Oct. 12, 2000.
Bito, Yoshitaka; Shintani, Yoichi; Sakata, Taiki; Matsuo, Hitoshi; "Method for Visualizing Multidimensional Data"; U.S. Appl. No. 09/687,058, filed Oct. 12, 2000; Publication Date: Aug. 7, 2001; pp. 1-25.

* cited by examiner

*Primary Examiner*—C Luke Gilligan
*Assistant Examiner*—R. David Rines
(74) *Attorney, Agent, or Firm*—Reed Smith LLP; Stanley P. Fisher, Esq.; Juan Carlos A. Marquez, Esq.

(57) ABSTRACT

There is provided a process analysis method capable of clustering of executed processes and extraction of similar processes.

A process analysis method of the present invention converts the similarity between processes into a numeric value as a metric by including a process matrix transform 12 and a metric calculation 14 for process records 11 made up of a series of records of rendered service of at least three elements of the time of service, the type of service, and the quantity of service. This enables the calculation of the similarity between processes as a metric from information of only a series of records of rendered services. Accordingly, it becomes possible to cluster the executed processes and to extract similar processes based on the metric herein calculated.

6 Claims, 8 Drawing Sheets

METHOD AND SYSTEM FOR CLINICAL PROCESS ANALYSIS

CROSS-REFERENCE TO RELEVANT APPLICATION

The disclosure of the patent application, Ser. No. 09/687,058, Filed on Oct. 12, 2000, pending in THE UNITED STATES Patent AND TRADEMARK OFFICE, has been incorporated by reference into the present application.

FIELD OF THE INVENTION

The present invention relates to software for analyzing electronically stored process records, a calculator or a storage medium storing the software, and an information system including the software. More particularly, it relates to software for analyzing a clinical process, a calculator or a storage medium storing the software, and a medical information system including the software in a medical field.

BACKGROUND OF THE INVENTION

In recent years, there has arisen a demand for a method capable of efficiently executing the planning, control, and analysis of a complicated clinical process for carrying out the optimum medical care. In order to respond to the demand, there is a proposed method of clinical pathway applying a critical pathway (Prior-art Example 1).

The clinical pathway is the schedule summarizing the routine work in clinical service, and defined as "a summary of admission guidance, admission orientation, laboratory test, medication, diet counseling, bed rest level, discharge guidance, and the like as a routine for a patient having a certain disease in a schedule". Further, the clinical pathway is a technique invented for an increase in efficiency of and standardization of clinical process. Originally, it derives from the process control technique in manufacturing industries referred to as a critical path method. As the process control techniques similar to the critical path method, there are the methods of PERT (Program Evaluation Review Technique) and Gantt Chart (Prior-art Example 2).

These methods exert their effects when the connection among respective operational services such as the order relationship among them is clear to a certain degree. However, in some of the processes targeted for the process analysis, the connection among respective services is not prescribed, or, in contrast, the connection among respective services must be derived from recorded processes. With the clinical process analysis in the medical field in recently increasing demand, the process in which the connection among respective clinical services is not clearly prescribed is often handled, so that it is difficult to prescribe the clinical services even to the details. This is because the disease, the patient status, the rendered clinical services, and the like are involved with the judgment of a physician complicatedly in each process.

The compliance of the performed clinical process to the clinical pathway is required to be analyzed continuously for the maintenance and the improvement of the quality of the clinical pathway. The analysis of the performed clinical process is useful for the determination of the effects and the improvement of the clinical process, the detection of an outlier, and the like even when the clinical pathway is not clearly shown. As analysis and reference methods of a clinical process being performed, in Japanese Published Unexamined Patent Application Nos. 10-214302 and 2000-348117, there are proposed medical treatment support systems in which the clinical process for each patient is displayed in a format of a table or in a format of a list (Prior art Example 3). Further, as one application of the analysis of the clinical process being actually performed, there is a proposed method for forming the prototype of the clinical pathway from the records of the performed clinical process. This method is described, for example, in Proceedings of the 17$^{th}$ Japan Joint Conference on Medical Informatics, on pages 140-141, issued in 1997 (Prior art Example 4). With this method, the prototype of the clinical pathway is formed from the statistics of clinical services for patients of similar cases. Incidentally, in the extraction of similar clinical processes and the classification of the clinical processes, the information of attributes included with the clinical process such as diagnosis and surgery is used, or the information classified according to the clinical service such as the information on execution or non-execution of a specific clinical service such as surgery is used.

With the foregoing prior-art technology such as PERT, Gantt Chart, or the critical path method (Prior-art Example 1), it has been difficult to calculate the similarity between processes when the relationship among services is not clearly described. For this reason, unfavorably, it has not been possible to easily perform the analysis of processes such as the classification of recorded processes or the detection of outliers.

In the medical field, particularly, the detailed relationship among clinical services is often not clearly described. Therefore, it has been difficult to calculate the similarity between clinical processes by using Prior-art Example 1 described above. Particularly, with a prior-art technology on the clinical pathway, an emphasis has been laid on the formation of the clinical process for each patient, so that sufficient consideration has not been given in regard to the analysis of the clinical processes for a plurality of patients. With the technologies disclosed in Japanese Published Unexamined Patent Application Nos. 10-214302 and 2000-348117, the display format by a text such as a table or a list is adopted in the reference method of the clinical processes. Therefore, unfavorably, it has been difficult to refer to and analyze a plurality of clinical processes. Whereas, in the foregoing technology on the formation of the clinical pathway from the clinical process records, described in Proceedings of the 17$^{th}$ Japan Joint Conference on Medical Informatics, the trend of the whole similar processes previously extracted according to the attribute is calculated. Thus, unfavorably, it has been difficult to perform a detail process analysis such as clinical process clustering therein. Further, it has not been possible to perform the classification according to the clinical services themselves, i.e., according to when and what has been done. Particularly, it is not possible to implement a detail case mix based on only the diagnosis and surgery, so that various cases are observed as analysis targets, making the analysis difficult.

An objective of the present invention is to provide a process analysis method enabling clustering the performed processes, and extracting similar processes even when the processes in which the relationships among services are not clearly described Further, it is another objective of the present invention to provide a process planning and control method applying such an analysis method. Still further, it is a still other objective of the present invention to provide an information system using these methods. Particularly, it is a further objective of the present invention to provide a clinical process analysis method capable of the clinical process clustering and the similar clinical process extraction, and a treatment plan/control support method in the medical field. It is a still more further object of the present invention to provide a medical information system using these clinical process plan, control, and analysis methods.

SUMMARY OF THE INVENTION

For solving the foregoing problems, a process analysis method of the present invention uses a metric calculation 14 for converting the similarity between processes into numerical data as a metric with respect to process records 11 made up of a series of records of rendered service of at least three elements of the time, type, and quantity of service as shown in FIG. 1. As a result, it becomes possible to numerically calculate the similarity between processes from information of only the records of rendered service even in the situation where the relation among respective services is not specified.

Particularly, when the method is intended for the analysis of a clinical process, the process analysis method of the present invention uses a metric calculation for converting the similarity between clinical processes into numerical data as a metric with respect to a series of records of treatment of at least three elements of the time of rendered clinical service, the type of clinical service, and the quantity of clinical service. As a result, it becomes possible to numerically calculate the similarity between clinical processes from information of only the records of treatment rendered on a patient.

In the metric calculation, assuming that the process is a function: $(T, J) \rightarrow R$, the metric is defined as the root of the square integral on to the function space. Herein, T denotes the time, J denotes the type, and R denotes the quantity (number of services, cost, revenue, measured value due to service, or the like).

Particularly, when the time can be discretely obtained, it is possible to regard the function as a two-dimensional matrix wherein (T, J) are axes, and to regard the metric as the metric in a (T×J)-dimensional space. The Euclidean metric may also be used as the metric in the (T×J)-dimensional space.

In the metric calculation method, as shown in FIG. 2, it is also possible that the metric is calculated as the root of the square integral after convolution of a broadening function on time-dimension. As a result, the shift of the process on time-dimension is allowed in accordance with the width of the convolution function. For example, when the Euclidean metric is used, the shift of the process on time-dimension and the execution of services of different types are calculated as the same difference in metric. However, when the calculation is performed after convolution of the broadening function on time-dimension, the shift of the process on time-dimension is calculated as a smaller difference in metric.

The convolution broadening function on time-dimension may also be configurable for every type of service. As a result, it is possible to change the shift allowance on time-dimension for every type. For example, it becomes possible to define such a shift allowance on time-dimension for every type that some services must be necessarily executed at a certain time point, but other services have an allowance in regard to the period for execution.

The metric calculation may also include a means for selecting a plurality of different metrics, so that an analyst can select the metric suitable for the objective of process analysis. Incidentally, for a plurality of the different metrics, the functions defining the metrics may be different from one another, or the form of the function defining the metric may change depending upon parameters.

The metric calculation may also be configured as follows. It includes a domain selection for selecting a part of or the whole of the time and type of service, which enables the analyst to select the type and time which the analyst is interested in. Thus, the metric is calculated by using only the records of rendered service belonging to the selected domain. As a result, it becomes possible to calculate the metric between processes under the situation where high-cost types are exclusively targeted, or the time is split.

There is included a means for clustering processes by using the metric between processes calculated by the metric calculation. As a result, it becomes possible to observe similar processes all together, and to extract outliers. Particularly, by clustering clinical processes, it becomes possible to provide case mix which was insufficient only by the patient information such as previously recorded diagnosis. This facilitates the clinical process analysis.

There is included a means for calculating the correlation between the process cluster calculated by using the process clustering means and the classification according to the previously recorded process attributes. This enables the correlation analysis that a process having a certain attribute tends to be included in a certain process cluster. For example, by calculating the correlation between the clinical process cluster and the patient attribute classification, it becomes possible to grasp the trend of treatment to be rendered on a patient having a certain attribute.

There is included a means for extracting the process group similar to a specific process by using the metric between processes being rendered. As a result, for example, it becomes possible to extract a patient group being rendered the similar treatment to a certain patient.

There is included a means for calculating the metric between processes, with respect to a specific process which has progressed partway, during a partial time until the time to which the process has progressed by using the process extraction, and extracting a similar process group. Alternatively, there is included a means for calculating the process cluster including a specific process by using the process clustering in place of extracting the similar process group. As a result, for example, it becomes possible to extract patients having the similar clinical process to the treatment rendered on a patient under treatment, and to help inferring the clinical process on and after that time, and forming the treatment plan.

A part of, or the whole of the process metric calculation, the process clustering, and the similar process extraction is included as a part of process analysis software. This offers mutual availability of the result with other components of the process analysis software, resulting in an improvement in analysis efficiency.

The software is applied in an information system. This enables execution via a network of the software, and acquisition and distribution of the execution results by the software.

The software is stored in a calculator or a storage medium to be executed or stored, transported, and supplied.

DETAILED DESCRIPTION OF THE PREFERRED EMBODIMENTS

Below, examples of the present invention will be described by reference to drawings.

Figure 1:
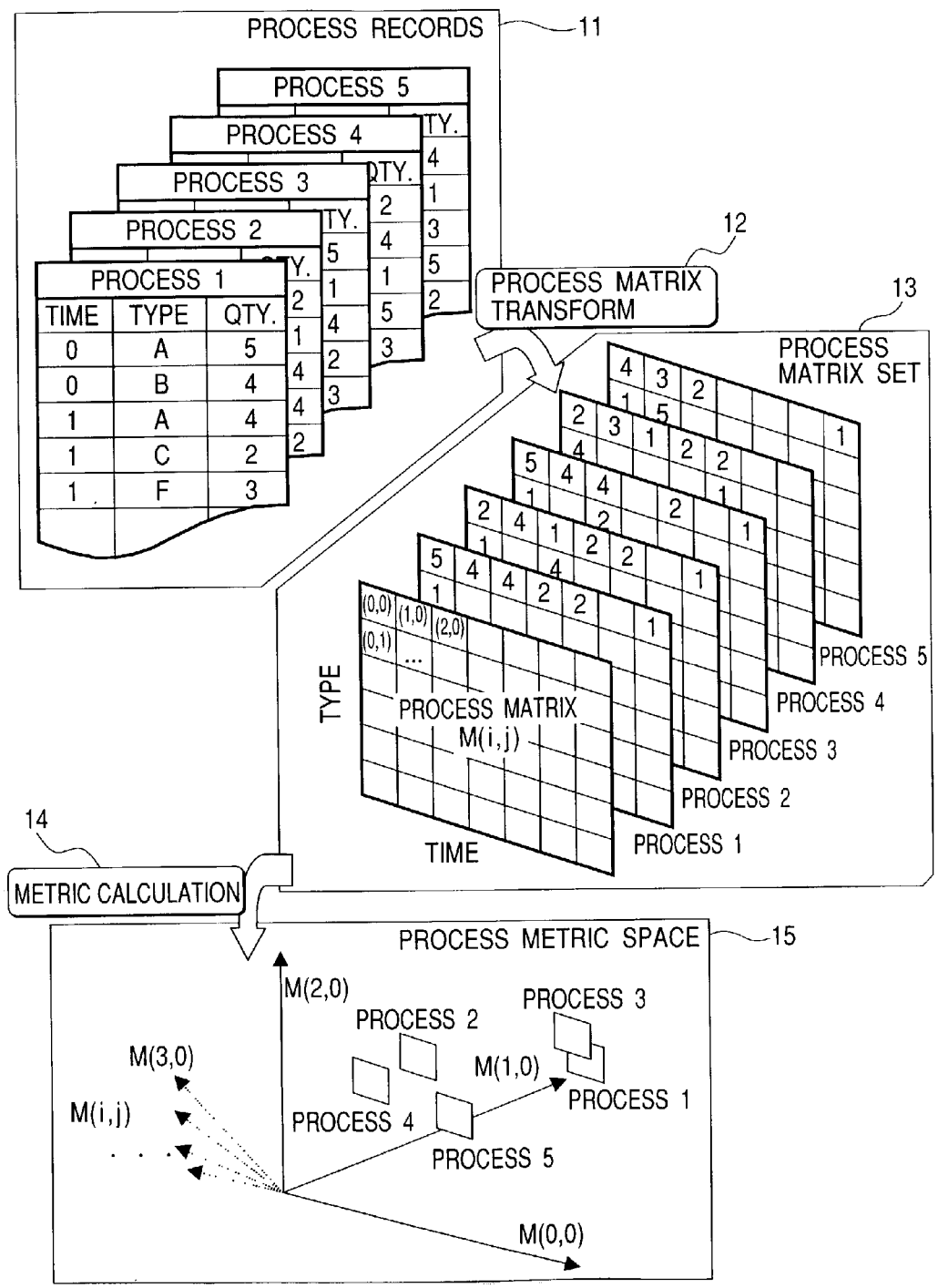
FIG. 1 is a conceptual diagram showing a method of calculation of the metric between processes of the present invention.

FIG. 1 is a diagram conceptually showing a method for introducing the metric between processes in a process analysis method of the present invention. Each process recorded in process records 11 corresponds to a series of records of rendered service composed of at least three elements of the time, type, and quantity of service. Herein, the quantity denotes the number of services, the cost of the service, the revenue and the profit resulting from the service, and the like. When the service relates to a measurement such as a laboratory test, the measured value may also be taken as the quantity. Further, the time of service may be not the time at which the service has been actually performed, but the time information in relation to the time at which the clinical service has been performed, for example, serial numbers given to a series of clinical services in time sequence.

In order to introduce a metric in between processes, first, respective processes are transformed to two-dimensional process matrixes in each of which the time and the type of service are used as axes by a process matrix transform 12 to form a process matrix set 13. Herein, the value indicated in each cell of the process matrix denotes the quantity of service. Then, onto a multidimensional space wherein respective elements M(i, j) of the process matrix are used as the axes, the metric calculated by a metric calculation 14 is introduced to construct a process metric space 15. As a result, it becomes possible to detect the similar processes, and to cluster the processes according to the metric.

Particularly, as an example of the process to be an object of analysis, mention may be made of a clinical process. When the clinical processes of inpatients are the objects of analysis, respective processes denote the records of the treatments of respective inpatients. The time represents the day from admission, and the type represents the type of the clinical service such as surgery, medication, or use of a medical room. The quantity represents the number and the cost of rendered clinical services, revenue, profit, or the like. Further, when the clinical service is a laboratory test or the like, the laboratory data may also be taken as the quantity. As a result, it is possible to define the metric for each clinical process rendered on inpatients. Accordingly, it is possible to detect the similar clinical processes and to cluster the clinical processes according to the metric.

Incidentally, the process matrix set 13 and the process metric space 15 of FIG. 1 represent their respective concepts, so that the processes are not required to be stored in such formats on a calculator. In the metric calculation 14, it is essential only that the operations displayed in this conceptual diagram are performed.

As the metric between processes calculated by the metric calculation 14, for example, a multidimensional Euclidean metric may be used. However, in this case, the shift of the process on time-dimension and the execution of different services have similar weights in calculation of the metric. However, in actuality, there is a high demand for the shift of the process on time-dimension has a higher similarity than that of the execution of difference services. For example, the difference in day of execution of clinical service of one or two days may happen according to the patient conditions or the allocation of hospital resource. Therefore, it often more matches the actual situation for the processes to be calculated as more, similar clinical processes than the case where different clinical services have been performed. For this reason, the process analysis method in accordance with the present invention includes a metric calculation as shown in FIG. 2.

Figure 2:
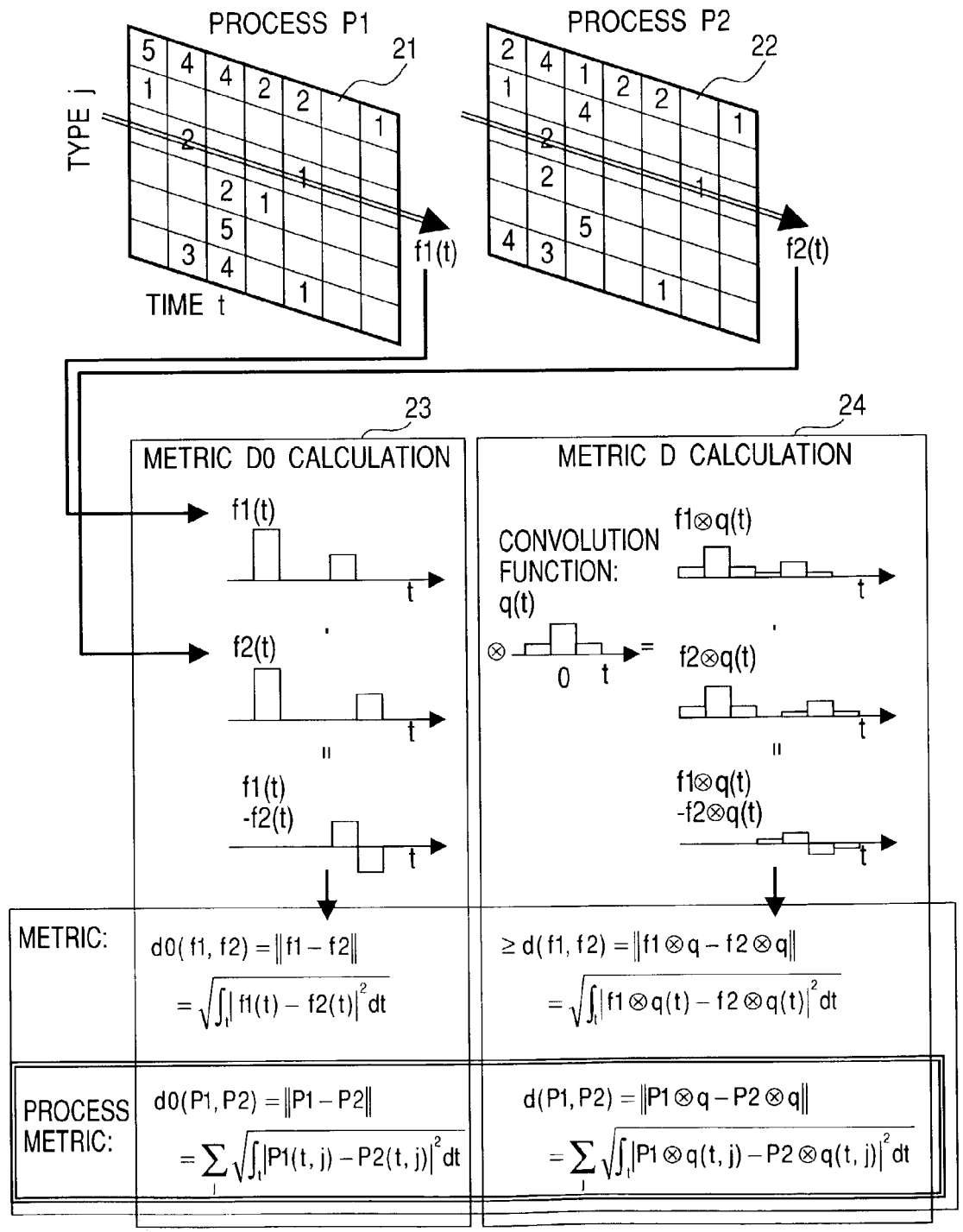
FIG. 2 is a diagram showing a method for calculating the metric having an allowance on time-dimension which is one example of the present invention.

FIG. 2 is a diagram showing the comparison between the case where the metric between a process P1 (21) and a process P2 (22) is calculated using the Euclidean metric (metric d0 calculation 23) and the case where the metric is calculated by convolution of a broadening function q on time-dimension (metric d calculation 24). For simplification of description, an attention is given on the type of a certain service, and a description will be given thereto by using functions f1(t) and f2(t) using profiles of the processes P1 and P2. Herein, the abscissa of each function denotes the time t and the ordinate denotes the quantity of service. With the metric d0 calculation 23, the difference between f1(t) and f2(t) is calculated, and the Euclidean metric d calculated as the root of square integral is calculated. In contrast, with the metric d calculation 24, a broadening function on time-dimension q(t) is convoluted with the f1(t) and the f2(t), and then the difference is calculated to calculate the root of the square integral. In this case, the f1(t) and f2(t) broadened by the function q(t) have a larger overlapping portion, and hence the metric d becomes smaller than the metric d0. Namely, in accordance with the metric d calculation 24, the metric is calculated to be shorter with respect to the shift of the process on time-dimension. Incidentally, the metric between the processes P1 and P2 is calculated by adding the metrics calculated for respective types with respect to all the types as shown in FIG. 2. Of course, in place of this, the following calculation may also be acceptable. The difference between the whole cells of the two-dimensional matrix, or the difference between the whole cells of the two dimensional matrix after convolution of the broadening function on time-dimension is calculated, to calculate the metric between the processes P1 and P2 as the root of the square integral. Further, for the discrete time, the integral described in the metric definition may also be changed to the summation for calculation.

Herein, by changing the convolution function q(t), it is possible to change the shift allowance of the process on time-dimension. For example, the broader the convolution function q(t) is, the more the shift allowance increases. When the function q(t) completely has a homogeneous broadening on time-dimension, the difference between processes due to the time of service is canceled.

As the convolution functions q(t), various functions are conceivable. For example, there are $q(t)=a \exp(-t^2/s^2)$, $q(t)=a \exp(-|t|/s)$, and the like. In these cases, by adjusting the parameter s, it becomes possible to adjust the shift allowance of the process on time-dimension. These functions do not have a finite support (i.e., the region of t in which the values other than 0 is not finite) However, the support of q(t) being finite allows more shortening of the calculation time. Further, such setting that the integral of q(t) becomes 1 offers an advantage in that the integral value of the convoluted function does not change, or other advantages. This namely means that the total number and the total cost of rendered services, and the like do not change.

Herein, the convolution function q(t) may also be changed for every type of service. As a result, it becomes possible to set the metric between processes in detail even in such a case where some services are required to have accuracy with respect to the shift of time, but other services have an allowance. Further, the convolution function q(t) may also be changed according to the time. As a result, for example, it becomes possible to cause the allowance with respect to the shift of the process on time-dimension to be generated increasingly with time.

Whereas, the convolution function q(t) may be not the function of only t, but the function q(t, j) of the time t and the type j. In this case, it becomes possible to allow the process to have an allowance in the direction of j. As a result, it becomes possible to set the metric between processes in detail even when there are similar types.

Further, as a method for calculating the metric in detail, there is also a method whereby an operator Q on the function space is used without convolution of the function q. The operator is an element on the function space, i.e., transform from one function to another function. The convolution of the function q is regarded as one operator.

Further, in the foregoing description, all of the time, type, and quantity of service were used in calculating the metric. However, it is also acceptable that the calculation is performed by using a part of them. Further, it is needless to say that other elements than these three elements may also be used. In this case, it is possible to calculate the metric by increasing the number of dimensions of the process matrix according to the added elements. Further, when some quantities of service are used, it is possible to calculate the metric in the foregoing manner only by changing the value filled in the cell of the process matrix from a one-dimensional real number to a multidimensional one.

As other definitions of the metric, mention may be made of the following ones. It is also possible to use pattern matching by dynamic programming for the calculation of the metric between the functions f1(t) and f2(t). As for the pattern matching by dynamic programming, an application example to speech analysis is proposed in Japanese Published Unexamined Patent Application No. Hei 8-16187. Further, in the calculation of the metric between the processes 1 and 2, it is also possible that the processes are regarded as two-dimensional images to calculate the feature values, and that the metric in the feature space is used. As for this, "Intelligent Image Processing", issued in 1994 from SHOKODO Co., Ltd., serves as a reference.

Further, the service not to be performed, the time during which service is not being performed, and the like may be present according to the process set to be an object of analysis. In this case, by calculating the metric excluding the corresponding service and time, it becomes possible to shorten the calculation time.

Further, it is also acceptable that, there are included a means for selecting a plurality of these metrics, and a means for setting parameters for prescribing the metrics, thereby providing a means for an analyst to select the metric suitable for the analysis.

Further, it is also acceptable that there is included a domain selection for narrowing down the time and type for calculating the metric. This is for setting the type and time which an analyst is interested in, and calculating the metric between processes using only the record of rendered services belonging to the type and time. The restricted metric calculation can be executed by restricting the integral range and the summation of the types to the selected portion. Inclusion of the domain selection enables easy calculation of the metric between processes by giving attention only to the high-cost types.

Incidentally, in the foregoing description by reference to FIGS. 1 and 2, the case of the discrete time was mainly taken. For the continuous time, by using the start/finish time stored in the process records, and the like, the process matrix M(t, j) is constructed as a function: (T, J)→R, and a metric is introduced into the function space. Herein, T denotes the continuous time; J, the type; and R, the quantity. As the metric, there may be used the metric obtained as the root of the square integral as the Euclidean metric as described above, and the metric obtained as the root of the square integral after convolution of the broadening function on time-dimension. It is needless to say that the definition of the broad function described for the discrete time, and the like are applicable to the case of the continuous time.

Further, the time and the type may also be respectively grouped in the process matrix transform of FIG. 1. For example, the time axis is set as a time zone, which may also be used as the column of the process matrix. Further, for the type axis, a group of types may also be appropriately formed to be used as the row of the process matrix.

Figure 3:
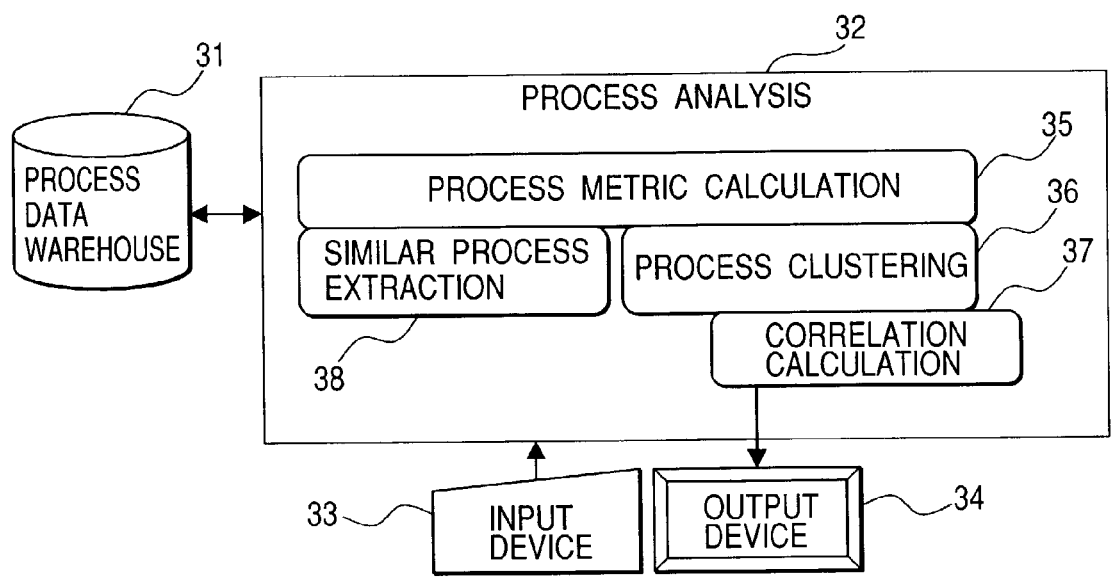
FIG. 3 is a schematic diagram of a configuration of a process analysis system including a process analysis method of the present invention.

FIG. 3 is a schematic diagram of a configuration of a system including the process analysis method in accordance with the present invention. A process analysis 32 extracts the process stored in a process data warehouse 31, performs processing in response to an input of an analyst from an input device 33, and outputs the result to an output device 34. The process analysis 32 includes the metric calculation 35, and calculates the metric between processes in accordance with the operation of the analyst. The process analysis includes a process clustering 36 for classifying the processes. With the process clustering 36, processes are clustered by using the metric calculated by the metric calculation 35. Of course, previously stored attributes may also be used in combination for clustering of the processes. As a result, it becomes possible to easily observe the trend of the processes, selectively observe outliers, and the like after clustering of the processes. Further, the process analysis 32 includes a correlation analysis 37 for calculating the correlation between the process cluster calculated by the process clustering 36 and the cluster according to the previously stored process attributes. As a result, it becomes possible to observe the correlation between the processes and the attributes, which facilitates the observation of the cause of the difference between the process clusters. Further, the process analysis 32 includes a similar process extraction 38 utilizing the metric calculated by the metric calculation 35 for extracting the similar processes to a specific process. Of course, the previously stored attributes may also be used for extraction of the similar processes. Incidentally, the metric calculation 35 in FIG. 3 is essential for this system. However, all of the three means of the process clustering 36, the correlation analysis 37, and the similar process extraction 38 are not necessarily required. Only a part of the components may be required to be included according to the analysis object or the necessary analysis results.

Figure 4:
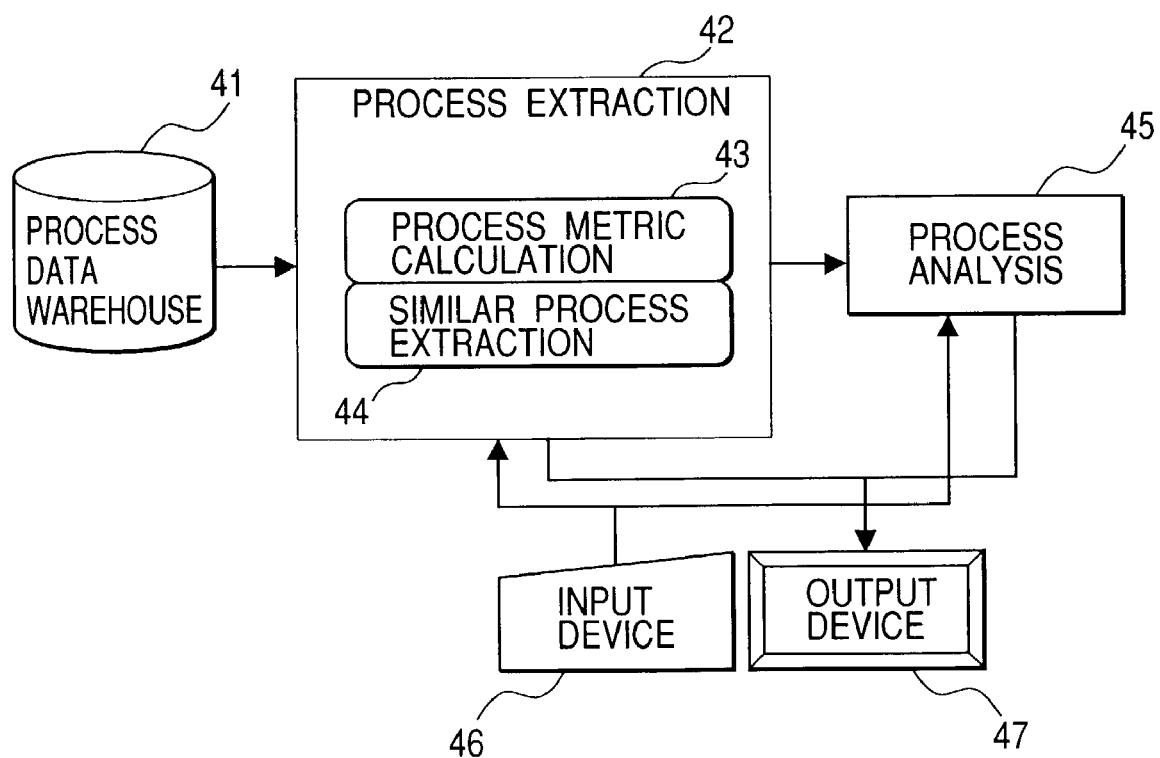
FIG. 4 is a schematic diagram of a configuration of a similar process extraction system including the process analysis method of the present invention.

FIG. 4 shows another example of the schematic diagram of a configuration of a system including the similar process extraction in accordance with the present invention. A process extraction 42 extracts the similar processes out of the processes stored in a process data warehouse 41 based on the information inputted from an input device 46, and passes them to a process analysis 45. Herein, the process extraction 42 includes a metric calculation 43. A similar process extraction 44 extracts the similar processes by using the metric calculated at the metric calculation 43. Of course, it is also possible to use not only the metric but also the previously stored process attributes for extraction of the similar processes. The process analysis 45 performs processing in response to the input from the input device 46, and produces an output to an output device 47. Incidentally, it is also possible that the process analysis 45 includes a part of, or all of the metric calculation 35, the process clustering 36, the correlation analysis 37, and the similar process extraction 38 described by reference to FIG. 3.

The process analysis method of the present invention will be further described in detail by taking the clinical process analysis for an inpatient as an example. For the clinical process analysis for an inpatient, the day from admission is used as the time, and the clinical service is used as the type.

Figure 5:
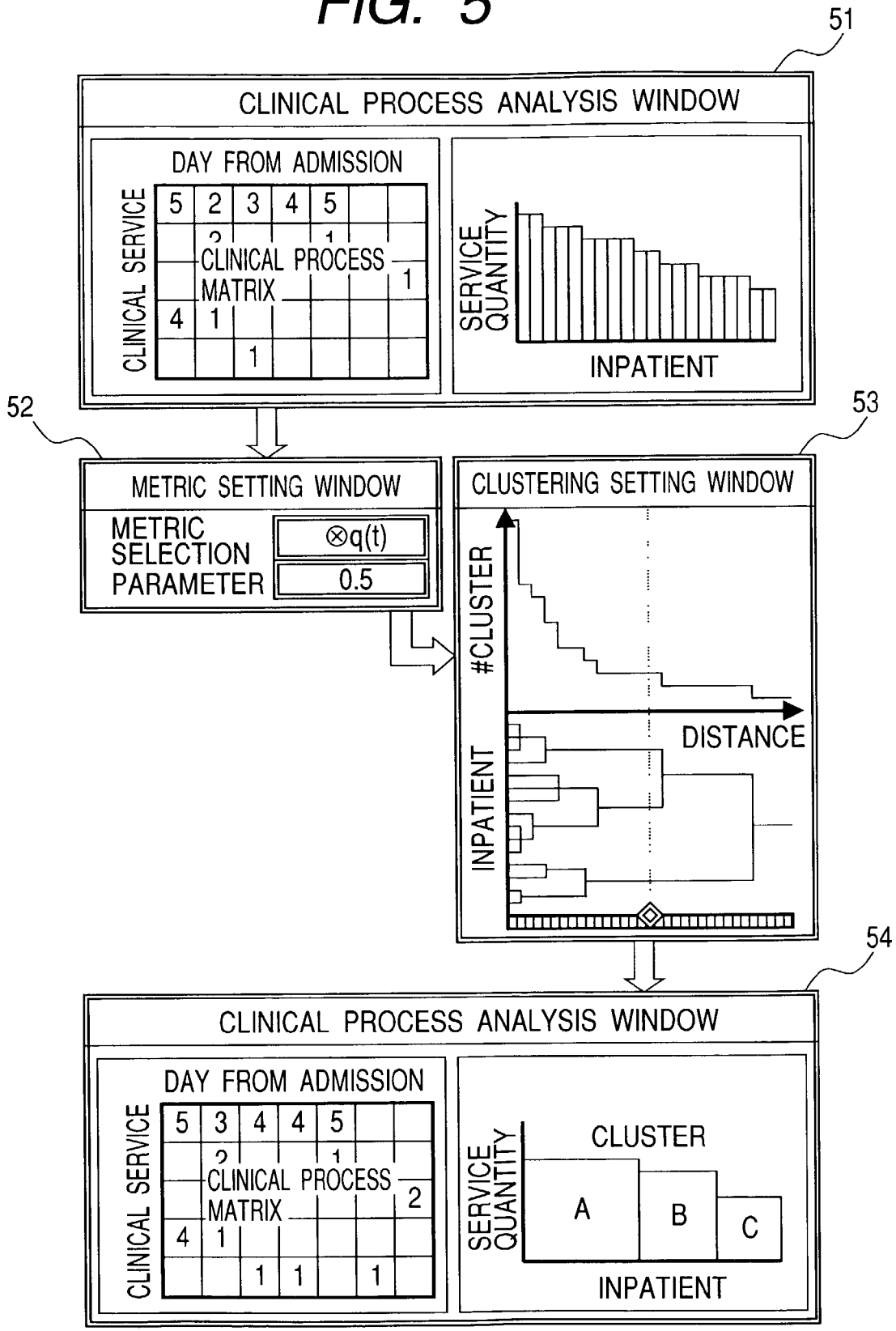
FIG. 5 is a flow chart showing a case where a process clustering of the present invention is applied to clinical process clustering of inpatients.

FIG. 5 is a flow chart illustrating the clinical process clustering by using screen examples out of the process analysis methods of the present invention. In the left-hand part of a clinical process analysis window 51, the clinical process matrix is drawn by expressing the quantity of service in gray level. However, in the chart, the numerical values are written as they are for convenience of display. In the right-hand part thereof, there is drawn a graph in which inpatients, i.e., respective clinical processes are plotted as abscissa, and the clinical service quantity as ordinate. Herein, in drawing the clinical process matrix, the average and the total sum of the clinical processes, and the like are drawn. For clustering the clinical processes, first, selection of a metric function and input of the parameter of the function are performed on a metric setting window 53. The preliminary result of clustering of the clinical processes is displayed in a clustering setting window 53 based on the set metrics. The distance is platted as abscissa. Thus, the graph in the upper part of the screen shows the number of clusters. Whereas, the graph in the lower part of the screen shows which clinical processes are included in the same cluster. A slider bar at the lowermost part of the screen is for setting the distance for clustering. When an analyst manipulates the slider bar to set the distance, the clinical processes are clustered based on the values, and the result is displayed in a clinical process analysis window 54. In this screen, inpatients in the right-hand part are displayed in classified form. It is noted that the clustering methods includes various methods. For example, the seeds for clustering may be set not in such a manner as to use only the foregoing metric as the parameter. The clustering setting window 53 shows one example, and the function and the arrangement thereof are not exclusive. Of course, it is needless to say that various functions and arrangements of the clinical process analysis windows 51 and 54, the metric setting window 52, and another window not shown, and the like are possible.

Figure 6:
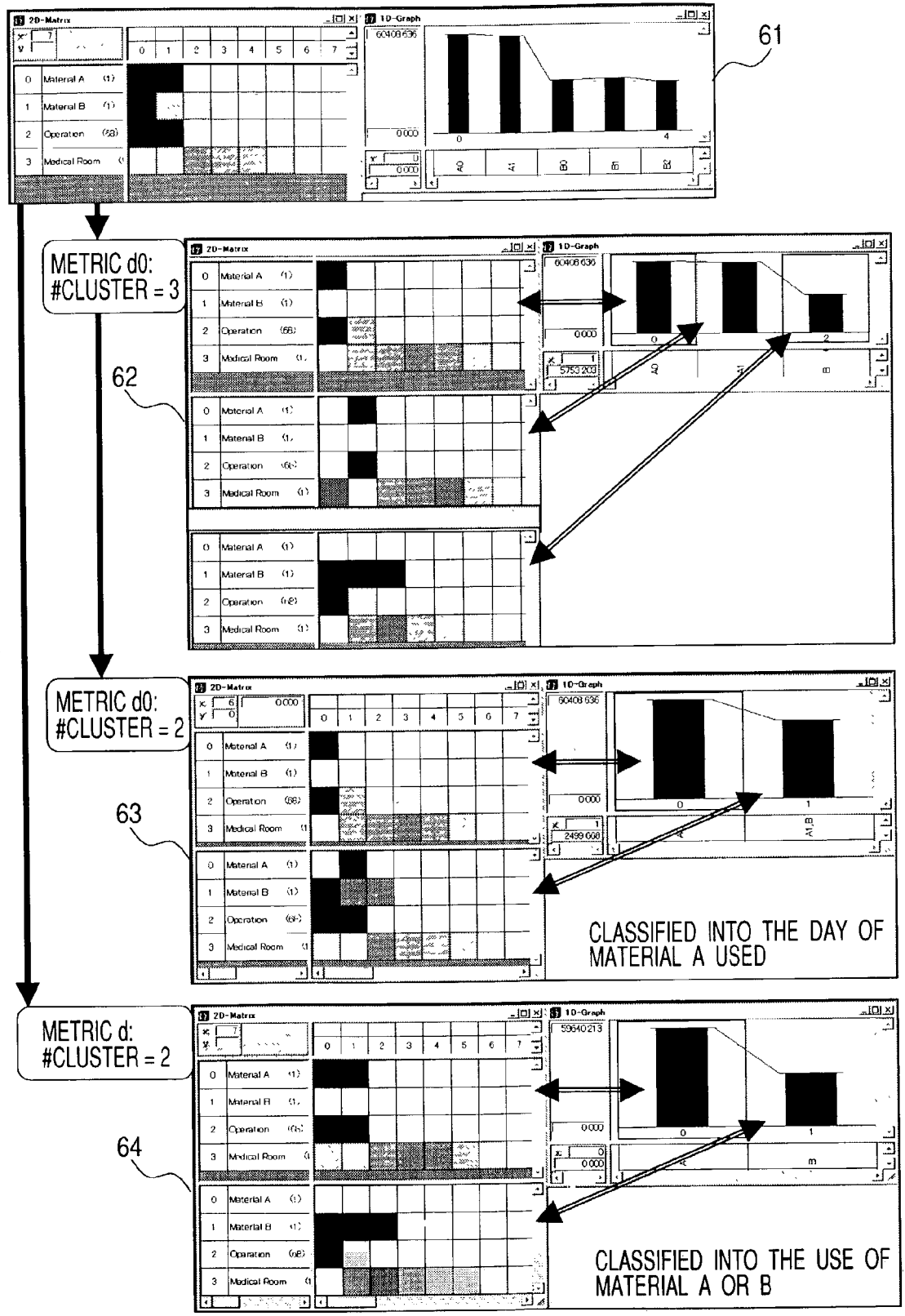
FIG. 6 shows an example wherein the process clustering of the present invention is applied to clinical process clustering of inpatients.

FIG. 6 shows the difference in clustering result between when the foregoing metric d0 is used and when the metric d having an allowance on time-dimension is used based on the clinical process records of inpatients. Herein, screens 61 to 64 denote clinical process analysis windows. In this chart, the cost of clinical service is used as the cell value. The blacker the color of a cell is, the higher cost the cell indicates. The service shown at the uppermost part denotes "use of Material A", and subsequently, "use of Material B". The screen 61 shows five clinical processes and the average clinical process matrix. The five clinical processes are: "a process in which the Material A is used on the first day from admission", "a process in which the Material A is used on the second day from admission", "a process in which the Material B is used on the first day from admission", "a process in which the Material B is used on the second day from admission" and "a process in which the Material B is used on the third day from admission". These are clustered by using the metric d0. First, when the number of clusters is set to be 3, these processes are clustered into three clusters of "a process in which the Material A is used on the first day from admission", "a process in which the Material A is used on the second day from admission", and "a process in which the Material B is used". Herein, the three screens in the left-side part draw their respective average clinical process matrixes. Further, when the number of clusters is set to be 2, these processes are clustered into two clusters of "a process in which the Material A is used on the first day from admission", and "a process in which the Material A is used on the second day from admission". However, in actuality, the difference in whether the Material A is used or the Material B is used often has a larger effect than the difference in whether the Material A is used on the first day or on the second day from admission. In this regard, when the processes are clustered by using the metric d having an allowance on time-dimension, they are clustered according to the difference in whether the Material A is used or the Material B is used, which matches this requirement.

Although it is needless to say that clustering of the clinical processes for inpatients in this manner facilitates the observation of the clinical processes, there are also various other advantages. For example, it becomes easier to detect a patient who has undergone a clinical process largely different from a normal one referred to as an outlier. Further, it becomes possible to perform detailed classification of cases unclassifiable only according to the diagnosis and the surgery. For example, the clustering method is also usable for determination of case mix such as Diagnostic Related Group (DRG). Further, calculation of the correlation with another classification according to patient attributes is useful for detection of the reason why the clinical process has been selected, and the like. Particularly, calculation of the correlation between clinical process clustering and diagnosis is useful for the determination of the diagnosis to a patient who has not received an accurate diagnosis. Further, storing of the calculated clinical process clusters as attributes in the clinical process data warehouse is effective for extraction of the similar clinical processes and an increase in speed of process analysis.

Figure 7:
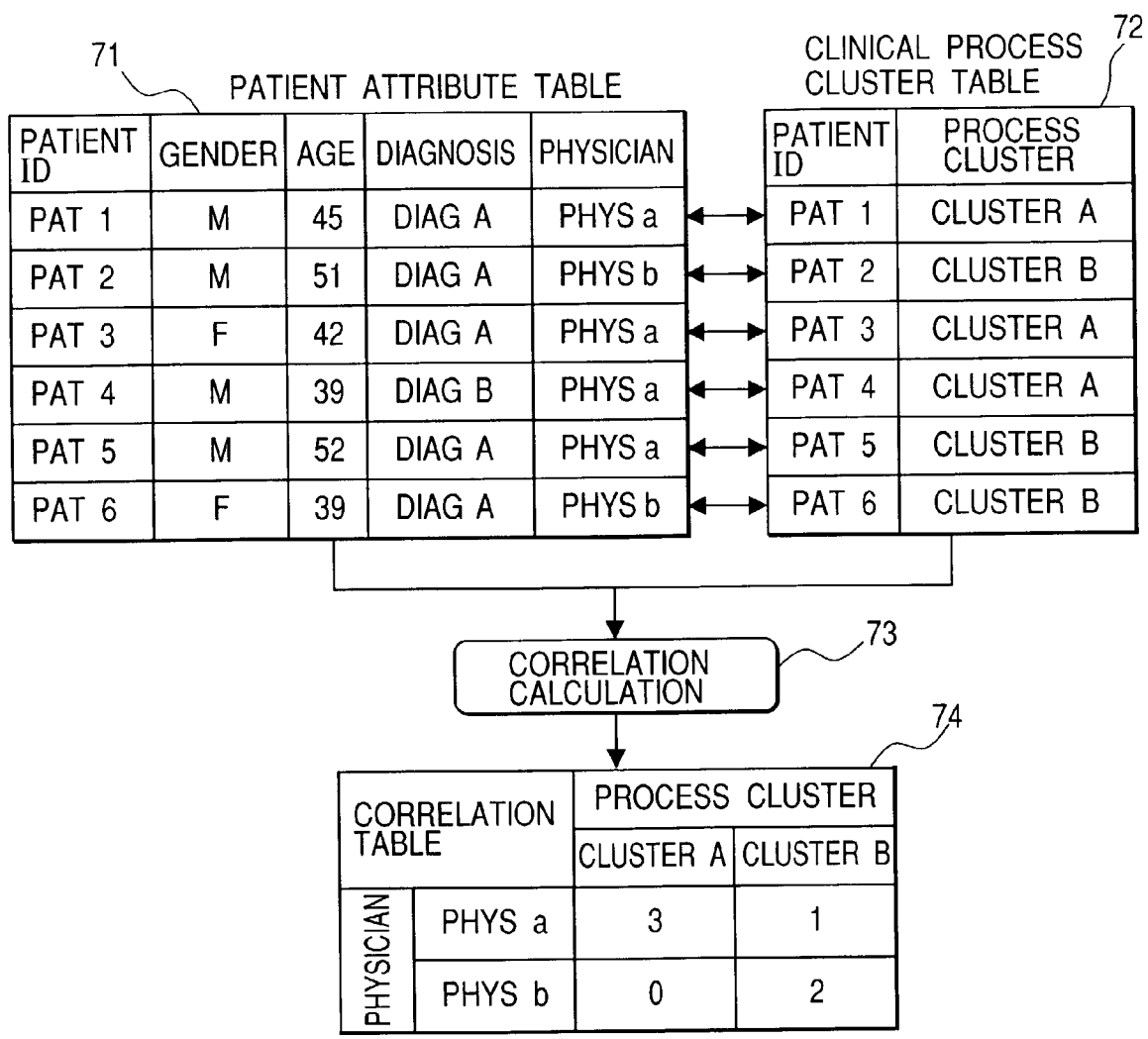
FIG. 7 is a flow chart for performing the correlation analysis between the execution results of the clinical process clustering of the present invention and the patient attributes.

FIG. 7 is a flow chart illustrating the correlation analysis between the cluster according to clinical processes and the classification according to the previously stored process attributes by using the result example in the process analysis methods of the present invention. In a patient attribute table 71, attributes such as gender, age, diagnosis, and physician are stored by using the patient ID as a key. The clinical process clusters calculated by the foregoing clinical process clustering is stored in a clinical process cluster table 72. Thus, a correlation table 74 with the classification according to the patient attributes is calculated by the correlation calculation 73. In the correlation table 74, the calculation results of the correlation coefficients between the physicians and the clinical process clusters are described. As a result, it becomes possible to know the correlation between the physicians and the process clusters. In consequence, such a rule that the event that "if the physician is a physician A, the clinical process is included in the cluster A" has a support of 3, and a confidence of 75% is derived. It is also possible for the component which derives a rule in this manner to be included in the process analysis method. Further, it is also possible for other decision support technique to be included in the process analysis. Particularly, the technique for extracting information from a large amount of data such as the foregoing clustering is referred to as data mining, and it is often used in decision support. As for this technique, for example, "Data Mining Technique", published from KAIBUNDO, 1999 serves as a reference.

Figure 8:
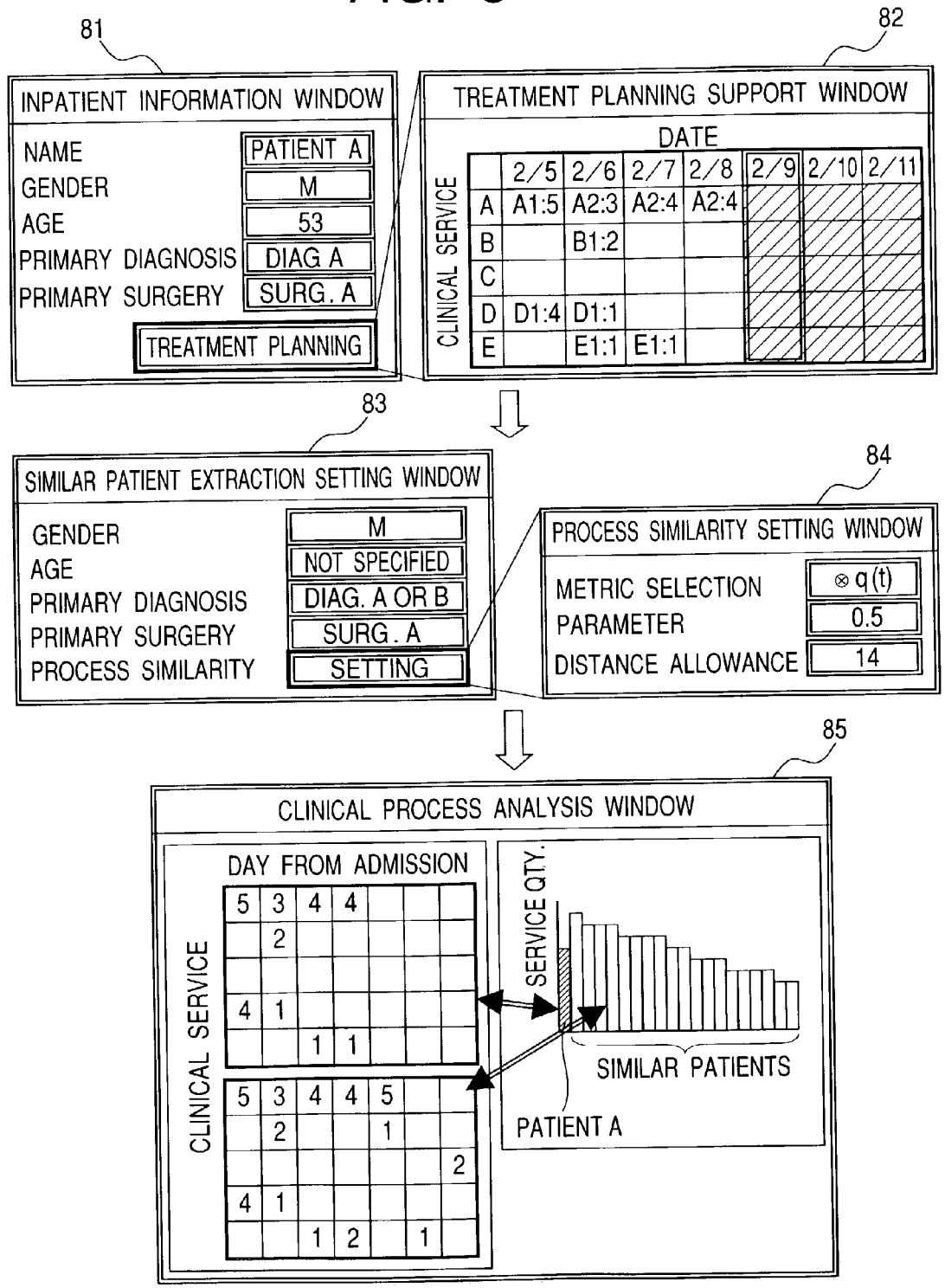
FIG. 8 is a flow chart showing a case where a similar process extraction of the present invention is applied to a treatment plan support.

FIG. 8 is a flow chart illustrating a treatment planning support using the similar clinical process extraction out of the process planning, control, and analysis methods in accordance with the present invention by using screen examples. In an inpatient information window 81, name, gender, age, primary diagnosis, primary surgery, and the like are described. Upon touch of a button for treatment plan, a treatment planning support window 82 is opened. The treatment plans from admission and the clinical results are described therein. In this example, the treatment progress until 2/8 is described, and the situation where the treatment plan on and after 2/9 is formed is assumed. A similar patient extraction setting window 83 is opened for selecting the similar clinical processes to be accessed, and parameters are inputted. Herein, it is possible to set the process similarity other than restriction of the patient attributes. A process similarity setting window 84 is opened for setting the process similarity. Then, the inputs of the metric selection for use and the parameter, and the allowable value of the metric for extraction of similar processes are set. The extracted similar processes are drawn together with a patient whose treatment plan is being formed in a clinical process analysis window 85. Herein, the matrix in the upper-left part shows the average clinical, process of a patient treatment planning, and the matrix in the lower-left part shows that of similar patients. It becomes possible to enter the treatment plan on and after 2/9 in the treatment planning support window 82 with reference to this. Herein, the following configuration is also acceptable. The standard treatment plan estimated from the average clinical process is automatically described in the treatment planning support window, so that a planner is only required to correct it. Further, the following configuration is also acceptable. The similar patient extraction setting, the process similarity setting, and the like are previously set to be standard ones, so that a standard treatment plan can be obtained at one step. The extraction of similar patients may also be accomplished in the following manner. The clustering according to the clinical process is previously performed, so that clinical process clusters having a high possibility of receiving a patient under treatment planning are extracted. Still further, the following configuration is also acceptable. Clinical process clustering is previously performed to form a critical pathway for every cluster, so that the critical pathway which may include a patient under treatment planning is extracted in place of extracting the similar clinical processes. Incidentally, this chart shows one typical example, and the function and configuration of the screen are not limited thereto.

Other application examples of the process analysis method of the present invention include customer analysis and consumer analysis. For example, there is a demand for classifying consumers according to not only the attributes such as gender and age, but also according to the mode of action to perform detailed marketing. In this case, the types indicating the mode of actions such as commutation, working, and use of a television are used as the types of service, and the day of the week and the time of the day are used as the times. Thus, when and what actions each individual took is recorded to obtain process records. In accordance with the present invention, it is possible to classify individuals according to the mode of action from the process records. Further, in accordance with the present invention, it is possible to perform the correlation analysis among the classification according to the mode of action, the classification according to the attributes such as age and job of an individual, the classification according to products to be bought, and the like. Further, adoption of a television program or the like as the type of the process record is useful for forming an effective advertisement broadcasting plan, or the like.

As described above, in accordance with the present invention, it becomes possible to calculate the similarities between the processes as metrics, which enables clustering of the processes according to the calculated metrics, and extraction of similar processes. Clustering of processes also produces an effect of simplifying the process observation, and enabling the correlation analysis with the process attributes. Accessibility to similar processes also produces an effect of allowing easy formation of the process plan. Particularly, in the clinical process analysis in the medical field, these effects are noticeable.

It is noted that the present invention can also be constituted by way of the following embodiment.

An information system includes a data warehouse in which clinical processes each including the time information of rendered clinical service, the type of clinical service, and the quantity of clinical service are stored; a means for reading the time information, the type of clinical service, or the quantity of clinical service from the data warehouse; a means for specifying a given process stored in the data warehouse; and a means for calculating a plurality of matrixes from the time information, the type of clinical service, and the quantity of clinical service in the clinical process stored in the data warehouse, arranging each matrix element of the plurality of the matrixes on a multidimensional space in which the row number and the column number $M(i, j)$ of each of the calculated matrixes are used as the axes to form a process metric space, and calculating the metric between the specified processes on the process metric space.

What is claimed is:

1. A process analysis method for estimating the similarity between at least two clinical processes, comprising the steps of:

forming a plurality of two-dimensional clinical process matrixes each of which maps rendered clinical service quantity data for one clinical process into cells coordinated by an axis marked by types of rendered clinical services and another axis marked by points in time t when the clinical services are rendered, respectively, and each of the cells containing a rendered clinical service quantity of a j type of rendered clinical services at an i time point is set to be as a matrix element $M(i, j)$;

calculating a similarity between at least two clinical processes each defined by a metric by selectively extracting between the respective matrix elements therein the and estimating the similarity between at least two of said clinical processes by using the calculated similarity between said clinical processes, wherein the similarity between said clinical processes is estimated, using a computing device having a processor, by the steps of:

profiling said clinical processes into functions defined by said selectively extracted respective matrix elements;

convoluting said functions with a broadening function on a time-dimension which corresponds to said points in time when the clinical services are rendered;

calculating differences of the convoluted functions;

calculating a root of square integral of the differences thereby estimating the similarity between said at least two of said clinical processes;

extracting a similar clinical process group among said at least two clinical processes based on said estimated similarity between said at least two clinical processes thereby establishing a treatment plan or a clinical pathway which consists of clinical processes that are determined to provide optimal healthcare options and which is presented in a schedule summarizing clinical services conducted during said clinical processes.

2. The process analysis method according to claim 1, further comprising: arranging each matrix element $M(i, j)$ of the plurality of the matrixes onto a multidimensional clinical process metric space by a metric calculation.

3. The process analysis method according to claim 1, wherein the broadening function is $q(t)=a \exp(-t^2/s^2)$ or $q(t)=a \exp(-|t|/s)$, parameter s is adjusted to shift allowance of a clinical process on the time-dimension.

4. The process analysis method according to claim 1, wherein the broadening function $q(t)$ is changed for different types of clinical services.

5. An information system, comprising:
a process data warehouse which stores a plurality of clinical processes having at least a time, type and quantity of rendered service;
an input device which inputs information of a process of interest;
a process extraction unit which extracts similar processes stored in the process data warehouse each as a similar process which is similar to the process of interest;
a process analysis unit including a metric calculation unit and a group process extraction unit; and
an output device,
wherein said metric calculation unit transforms said process of interest in conjunction with one of said processes into two-dimensional process matrixes in each of which points of time when the services are rendered and types of service are used as axes, convolutes said two-dimensional process matrixes with a broadening function on a time-dimension,
calculates a distance between said process of interest and said one process by calculating a root of a square integral of differences between the convoluted two-dimensional process matrixes as a distance in-between thereby estimating a similarity between said process of interest and said one process,
extracts a group of similar processes from the plurality of processes, if said distance between said process of interest and said each process is shorter or equal to a predetermined value, so as to establish a treatment plan or a clinical pathway which consists of clinical processes that are determined to provide optimal healthcare options and which is presented in a schedule summarizing clinical services conducted during said clinical processes, and
wherein said output device displays said extracted group of similar processes.

6. The information system according to claim 5, wherein said process analysis unit further includes a process clustering unit,
wherein said process clustering unit clusters said group of similar processes based upon distances between said process of interest and each of said group of similar processes, and
wherein said output device displays a result of clustering.

* * * * *